United States Patent
Tardy et al.

(10) Patent No.: US 11,941,803 B2
(45) Date of Patent: Mar. 26, 2024

(54) SYSTEM AND METHOD FOR PROCESSING AT LEAST ONE POLLUTING REGION OF A DIGITAL IMAGE OF AN OBJECT EXPOSED TO X-RAYS

(71) Applicant: HERA-MI, Nantes (FR)

(72) Inventors: Mickael Tardy, Nantes (FR); Bruno Scheffer, Nantes (FR)

(73) Assignee: HERA-MI, Nantes (FR)

( * ) Notice: Subject to any disclaimer, the term of this patent is extended or adjusted under 35 U.S.C. 154(b) by 613 days.

(21) Appl. No.: 17/253,179

(22) PCT Filed: Jun. 18, 2019

(86) PCT No.: PCT/FR2019/051487
§ 371 (c)(1),
(2) Date: Dec. 17, 2020

(87) PCT Pub. No.: WO2019/243731
PCT Pub. Date: Dec. 26, 2019

(65) Prior Publication Data
US 2021/0264594 A1    Aug. 26, 2021

(30) Foreign Application Priority Data

Jun. 19, 2018    (FR) ...................................... 18 55390

(51) Int. Cl.
*G06T 7/00*         (2017.01)
*A61B 6/00*         (2006.01)
(Continued)

(52) U.S. Cl.
CPC ............ *G06T 7/0012* (2013.01); *A61B 6/502* (2013.01); *A61B 6/5217* (2013.01); *G06T 7/11* (2017.01);
(Continued)

(58) Field of Classification Search
CPC ....... G06T 7/11; G06T 7/0012; G06T 11/001; G06T 5/00; G06T 2207/10116;
(Continued)

(56) References Cited

U.S. PATENT DOCUMENTS

| 5,671,263 A * | 9/1997 | Ching-Ming ......... G01T 1/1648 378/98.2 |
| 2016/0133033 A1* | 5/2016 | Highnam .............. G06T 11/008 382/131 |
| 2020/0240934 A1* | 7/2020 | Yi ......................... G06T 11/008 |

OTHER PUBLICATIONS

International Search Report dated Nov. 8, 2019.
(Continued)

*Primary Examiner* — Congvan Tran
(74) *Attorney, Agent, or Firm* — IPSILON USA, LLP

(57) ABSTRACT

The invention relates to a system and method for processing a polluting region of a digital image of an object (3) acquired using X-rays and comprising points (P) with each of which there is associated a numerical intensity value and at least one item of metadata (M) chosen from among one or more physical parameters of the object, and one or more parameters relating to the power or the energy of the X-rays with which the image was acquired. Said method comprises identifying at least one group of points in the image corresponding to a polluting region on the basis of the initial intensity values $I_0$ of the points in the image and of said metadata. Generating a new image comprises a step of replacing the initial intensity values $I_0$ of at least some of the points of said at least one polluting region with new intensity values.

20 Claims, 8 Drawing Sheets

(51) Int. Cl.
 *A61B 6/50* (2024.01)
 *G06T 7/11* (2017.01)
 *G06T 11/00* (2006.01)
(52) U.S. Cl.
 CPC ... *G06T 11/001* (2013.01); *G06T 2207/10116* (2013.01); *G06T 2207/20021* (2013.01)
(58) Field of Classification Search
 CPC . G06T 2207/20021; G06T 2207/30068; A61B 6/5217; A61B 6/502
 See application file for complete search history.

(56) References Cited

OTHER PUBLICATIONS

He Wenda et al. "Breast image pre-processing for mammographic tissue segmentation" Computers in Biology and Medicine, New York, NY, US, vol. 67, Oct. 14, 2015 (Oct. 14, 2015).
Wenda He et al. Mammographic Segmentation and Risk Classification Using a Novel Binary Model Based Bayes Classifier, Breast Imaging, Springer Berlin Heidelberg, Berlin, Heidelberg, pp. 40-47. Jul. 8, 2012.
Chinese Office Action Notification dated Feb. 21, 2023.

\* cited by examiner

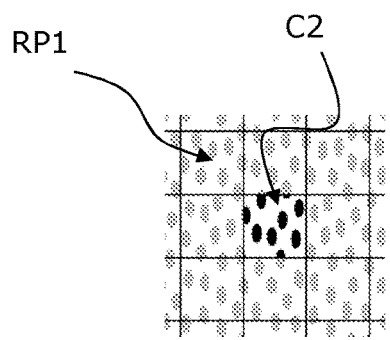
FIG.12
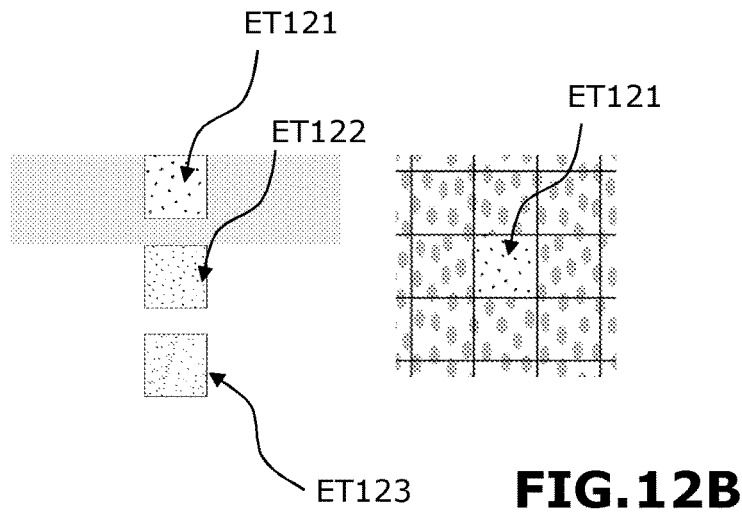
FIG.12A FIG.12B
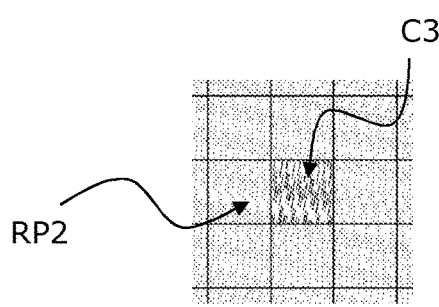
FIG.13
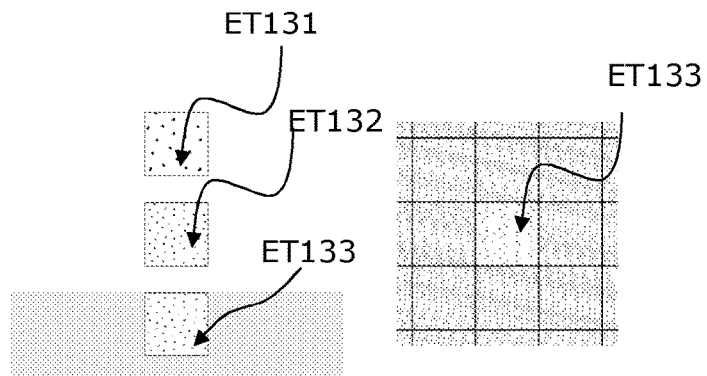
FIG.13A FIG.13B

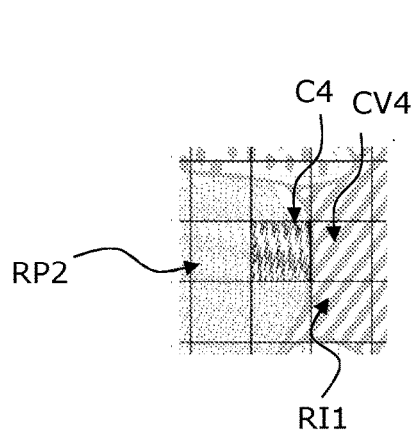 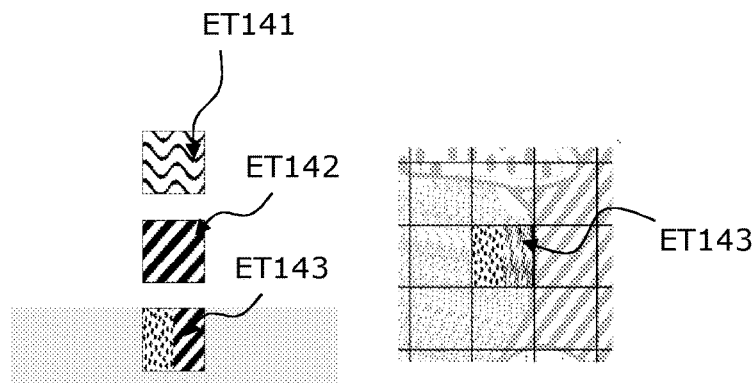
FIG.14  FIG.14A  FIG.14B
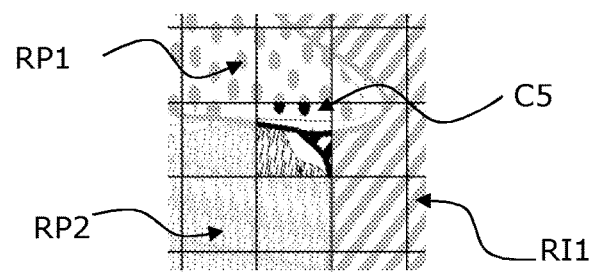
FIG.15
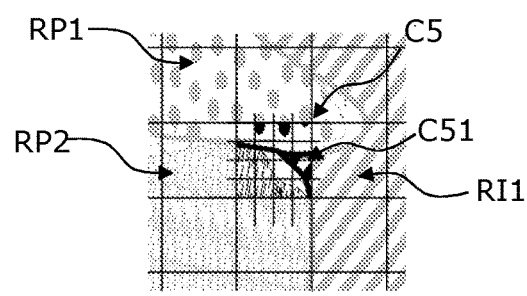
FIG.15A

SYSTEM AND METHOD FOR PROCESSING AT LEAST ONE POLLUTING REGION OF A DIGITAL IMAGE OF AN OBJECT EXPOSED TO X-RAYS

RELATED APPLICATION

This application is a National Phase of PCT/FR2019/051487 filed on Jun. 18, 2019 which claims the benefit of priority from French Patent Application No. 18 55390, filed on Jun. 19, 2018, the entirety of which are incorporated by reference.

FIELD OF THE INVENTION

The present invention relates in general to a computer system, to an installation and to a method for processing images.

PRIOR ART

In the field of medical radiography, and in particular in the field of mammography, a radiologist has to be able to reliably interpret the image corresponding to the X-ray that is taken in order to detect any anomalies in the object that is X-rayed.

The image corresponding to a mammogram may comprise one or more regions, called regions of interest, which may exhibit anomalies corresponding to pathologies.

These regions have to retain the radiologist's attention while other regions, called regions of non-interest or polluting regions, correspond to parts of the X-rayed object, for example to healthy linear structures (vessels, connective tissue), which are of no particular interest to the radiologist.

The presence of these regions may however hamper analysis of the image by the radiologist, and may in particular interfere with the identification of anomalies in a region of interest.

It is known to modify the polluting regions by applying an identical intensity value to the various points of the polluting region or even to increase the intensity of the regions of interest, but the result that is obtained is often unsatisfactory because such processing of the polluting region may also interfere with the radiologist's analysis and thus hamper his interpretation of the region(s) of interest.

The document "Breast image pre-processing for mammographic tissue segmentation" and document US2016133033A1 in particular disclose image processing methods that propose to modify or reconstruct an image acquired by mammography. However, these modification or reconstruction methods may also interfere with the interpretation of the radiologist's analysis.

The aim of the present invention is to propose a novel computer system, a novel installation and a novel method for mitigating all or some of the problems set out above.

SUMMARY OF THE INVENTION

To this end, the invention relates to a method, implemented using a computer system, for processing at least one part, called polluting region, of a digital image of an object, the image being produced from an X-ray apparatus by exposing the object to X-rays,
said image being stored in a data memory and comprising:
points with each of which there is associated a numerical intensity value, called initial intensity $I_0$, which corresponds to the number of photons that have struck a corresponding point of the object, and
at least one item of metadata,
characterized in that said at least one item of metadata comprises at least one of the following items of metadata:
one or more physical parameters of the object, such as the thickness of the object,
one or more parameters relating to the power or the energy of the X-rays with which the image was acquired, such as the voltage and electric current values used to produce the X-rays;
said method comprising:
identifying at least one group of points in the image corresponding to a polluting region on the basis of the initial intensity values I0 of the points in the image and of said at least one item of metadata;
generating a new image comprising a step of replacing the initial intensity values $I_0$ of at least some of the points of said at least one polluting region with new intensity values.

According to one particular aspect, the object is an organ of a human or animal body.

There may be provision for one or more parts, such as linear structures, of a polluting region of the image, in particular when this is a breast image, to be replaced with one or more image parts corresponding to less visually attractive areas, such as fatty areas.

The method may also comprise one or more of the following features, taken from any technically acceptable combination.

According to one advantageous feature of the invention, the method also comprises identifying at least one group of points in the image corresponding to a region of interest on the basis of the initial intensity values $I_0$ of the points in the image and of said at least one item of metadata.

According to one advantageous feature of the invention, the step of identifying at least one group of points in the image as a polluting region comprises comparing these points in the image with other groups of reference points stored in a database, each group of reference points being associated with at least one item of metadata, called reference item of metadata.

According to one advantageous feature of the invention, the method comprises providing a set of texturing elements stored in a data memory,
each texturing element comprising a plurality of points and intensity values associated with the points,
and the step of replacing the initial intensity values $I_0$ of at least some of the points of said at least one polluting region with new intensity values comprises:
selecting a texturing element from among a plurality of texturing elements or generating a new texturing element from one or more selected texturing elements,
replacing the initial intensity values $I_0$ of at least some of the points of said at least one polluting region with the intensity values of at least some of the points of the selected texturing element or of the generated new texturing element.

According to one particular aspect, each texturing element comprises at least one item of metadata and one or more texturing elements are selected on the basis of this item of metadata.

According to one particular aspect, in order to mask a group of points in the image identified as forming part of a polluting region, the method comprises selecting or generating a texturing element whose features (which may take the form of metadata, for example size data, value data or moment of intensity data, etc.) most closely match the features of the polluting region, with the obvious exception of the features corresponding to the tissue type in the polluting region.

The tissue type may be for example a vessel. A polluting region of healthy vessel type may thus be replaced with a texturing element whose tissue type is fat and whose features, other than the tissue type, are close to those of the original polluting region, to those of the adjacent regions, and/or to those of the entire original image.

According to some embodiments, the selected texturing element or the generated new texturing element has an item of metadata corresponding to a tissue type, for example fat, which is different from the tissue type, for example a blood vessel, of the polluting region to be replaced.

According to one advantageous feature of the invention, said at least one item of metadata associated with the image comprises an item of metadata defined by correlation with at least one part of another image of the object.

Said other image used for the correlation may be an image of said object, but acquired from another angle or at another time. Said at least one item of metadata may be for example the location, or the type of region, polluting region or region of interest, in particular when the correlation is performed by comparing images taken at different times.

According to one advantageous feature of the invention, for an identified polluting region, the method comprises:
  calculating at least one mathematical moment from the intensity values, such as the average intensity value $I_{avg}$ or the intensity variance, of the points in at least one part of said identified polluting region,
  selecting a group of points, called texturing element, from among a plurality of predefined texturing elements, or generating a new texturing element from a plurality of selected texturing elements,
  the texturing element being selected or generated on the basis of said at least one calculated mathematical moment, such as said average intensity value $I_{avg}$ or said intensity variance, of the points in said at least one part of the polluting region, the points of said selected texturing element or of said generated texturing element having a set of intensity values different from that of the points in said at least one part of said identified polluting region;
  and at least some of the points of said selected texturing element or of said generated new texturing element replace the points in said at least one part of the identified polluting region.

According to one particular aspect, the initial intensities of an area of the image (group of points), such as the points in a cell of the image, are used, through comparison with reference image samples, to assign at least one item of metadata to the points in this area, making it possible to classify the type of material in this area, for example a tissue type.

Next, this item of metadata, possibly with other data, is used to select, from among a set of predefined texturing elements, an appropriate predefined texturing element, or to generate a new texturing element from a plurality of selected predefined texturing elements, in order to replace the points in the original area of the image with the points of this texturing element.

The item(s) of metadata associated with an area of the image may thus make it possible to identify the physiological type of the area of the image and to choose at least one appropriate texturing element from among a plurality of texturing elements previously stored in a given base. Other metadata from said area of the original image may be used to make this selection, as explained below.

There may be provision for each stored texturing element to also itself be provided with metadata in order to make it possible to analyze the acceptability or lack thereof of this texturing element with respect to said area of the image with a view to replacing said area of the image.

The points that form this texturing element (and that have a set of predefined intensity values different from that of the points in said area of the initial image) are used to replace the points in said area of the initial image.

The replacement means that it is not a mathematical intensity processing operation that is applied to the image, as may be the case in the prior art, which could be reversible through an inverse operation, but rather an irreversible substitution of the points in said area of the image with other points originating from at least one texturing element that is external (or foreign) to the original image.

According to one particular aspect, there is no inverse mathematical transformation that makes it possible to recover the intensity values of the original points from the intensities of the points in the processed image that have replaced said original points. The use of a texturing element to replace the area in question is therefore distinguished from a simple processing operation on the intensities of the area because it involves a texturing element available separately from the image and selected from among a plurality of texturing elements, and possibly modified/adjusted, or a new texturing element generated from selected texturing element(s), and which replaces the area in question of the image.

Thus, by way of example and in particular in the case of an image of a breast, the points in an area of the image may have initial intensity values that make it possible, possibly in combination with other data, to identify that it is part of a healthy vessel. This identification may be carried out using a statistical learning algorithm using for example shape and/or intensity deviation features to conclude as to the tissue type. An item of metadata corresponding to a healthy vessel may then be associated with the points in this area of the image.

By way of example, the texturing element may comprise, as metadata, the location, in the object, of the material that corresponds to this texturing element. Thus, when the texturing element corresponds to fatty tissue, an additional item of metadata may specify that it is subcutaneous fat.

According to one particular aspect, the region(s) of interest are not replaced with texturing elements.

This item of metadata for the points in the area, possibly in combination with other data, then makes it possible to select an appropriate texturing element whose points are then used to replace the points in the area of the original image.

A texturing element with which there is associated an item of metadata representative of the fact that the features of this texturing element correspond to fat may thus be selected from among a plurality of texturing elements to replace the area of the original image corresponding to said healthy vessel part, so as not to draw the radiologist's eye to this area of the image, while at the same time keeping the realistic and familiar visual appearance of the breast for the radiologist's eye.

It is specifically understood that, in the image, a healthy vessel is a region that is of no interest to the radiologist and would risk polluting his analysis if it were to remain present as it is in the image. Simply modifying the image, for example by increasing the intensity values of other areas, would still run the risk of hampering the radiologist. Similarly, simply normalizing the intensity values would not be sufficient. Replacing this area of the vessel with a texturing element selected on the basis of the features of this area of the vessel makes it possible to preserve a natural image of the breast while at the same time preventing the radiologist's eye from being drawn to this area. The radiologist is thus able to naturally concentrate on the other area(s) that are identified as areas of interest.

There may be provision for the intensities of the points of the texturing element selected to replace the original points to be further modified on the basis of features or metadata (such as a moment of intensity, a classification parameter) of groups of adjacent points in order to ensure continuity or a smooth visual transition between the replaced area and the adjacent area(s).

In other words, for an area corresponding to at least one part of a polluting region, a texturing element is selected or generated from selected texturing elements, the features of which texturing element, in particular its intensity, make it possible to replace the points in the area with the points of said texturing element that is compatible with keeping the realistic appearance of the object (for example a breast) of the image thus modified, while at the same time reducing the drawing of the operator's eye to this area so that he is able to concentrate on other areas of real interest.

According to one advantageous feature of the invention, said replacement step, also called masking operation, comprises breaking the image of the object down into blocks of adjacent points, called cells.

According to one particular aspect, when each of the points in a cell belongs to a region of interest, said points remain unchanged in the generated new image.

According to one advantageous feature of the invention, when the points in a cell belong to a polluting region and the points in the adjacent cells also belong to said polluting region, said points in the cell are replaced with the points of a texturing element chosen from among a plurality of predefined texturing elements.

According to one particular embodiment, the selection of said texturing element from among said plurality of predefined texturing elements depends on the intensity values of said points in the cell.

According to one advantageous feature of the invention, when the points in a cell belong to a polluting region and points in at least one adjacent cell belong to a category other than said polluting region, for example to a region of interest or to another polluting region, a new texturing element is generated from at least one, preferably a plurality of, predefined texturing elements, and on the basis of the points in said at least one adjacent cell, the points in said cell being replaced with the points of said new texturing element.

According to one advantageous feature of the invention, when a cell contains both points of a region of interest and of a polluting region, the cell is broken down into sub-cells, which may themselves be broken down into sub-cells until each sub-cell contains only points of a region of interest or only points of a polluting region.

According to one advantageous feature of the invention, the method comprises a step of processing the acquired image in which the part of the image corresponding to the object, called image of the object, is isolated from the background of the acquired image.

According to one advantageous feature of the invention, the method comprises a step of determining a region, called contour region, corresponding to a contour area of the object.

According to one advantageous feature of the invention, the method comprises identifying, in the image part corresponding to the object, at least one geometric structure, for example a linear structure. The method comprises assigning said at least one identified geometric structure a classification parameter having a first value, corresponding to a category of interest, when a correlation is established between said geometric structure and at least one region of interest; and a second value, corresponding to a category of non-interest, when there is no correlation between said geometric structure and the region(s) of interest.

According to one advantageous feature of the invention, with the object being able to be compressed under the effect of a given compressive force, said at least one item of metadata comprises the thickness of the object in the compressed state and the compressive force applied to the object.

The invention also relates to a non-transient computer program product comprising program code instructions for executing the steps of a method as proposed above when said program is executed by a processor of a computer system.

The invention also relates to a recording medium on which the computer program is stored.

The invention also relates to a computer system comprising a memory containing program code instructions for executing the steps of a method as proposed above, a processor for executing said program code instructions, a memory for storing image data and metadata, and preferably a display screen.

The invention also relates to an installation comprising a computer system as proposed above, and an X-ray apparatus, said apparatus comprising an emitter device able to emit an X-ray beam and a receiver device able to receive the X-rays emitted by the emitter device after they have passed through the object, and the X-ray apparatus being configured so as to transmit, to the computer system, image data corresponding to the X-rays received by the receiver device after they have passed through the object, and optionally metadata comprising for example one or more parameters relating to the power or to the energy of the X-rays produced.

BRIEF DESCRIPTION OF THE DRAWINGS

Other features and advantages of the invention will become more apparent from the following description, which is purely illustrative and non-limiting and should be read in conjunction with the appended drawings, in which:

FIG. 12 is a view of part of the image from FIG. 10 showing a cell C2 of a first polluting region and adjacent cells, according to one embodiment of the invention;

FIG. 12A is a schematic view showing a plurality of texturing elements according to one embodiment of the invention;

FIG. 12B is a schematic view of the image part from FIG. 12 after modification of the cell C2 on the basis of at least one texturing element from FIG. 12A, according to one embodiment of the invention;

FIG. 13 is a view of part of the image from FIG. 10 showing a cell C3 of a second polluting region and adjacent cells;

FIG. 13A is a schematic view showing three texturing elements according to one embodiment of the invention;

FIG. 13B is a schematic view of the image part from FIG. 13 after modification of the cell C3 on the basis of at least one texturing element from FIG. 13A, according to one embodiment of the invention;

FIG. 14 is a view of part of the image from FIG. 10 showing a cell C4 of a polluting region and adjacent cells, according to one embodiment of the invention;

FIG. 14A is a schematic view showing three texturing elements, one of which (the one at the bottom) has been generated on the basis of the other two, according to one embodiment of the invention;

FIG. 14B is a schematic view of the image part from FIG. 14 after modification of the cell C4 on the basis of the generated texturing element from FIG. 14A, according to one embodiment of the invention;

FIG. 15 is a view of part of the image from FIG. 10 showing a cell C5 comprising region of interest points and polluting region points, according to one embodiment of the invention;

FIG. 15A is seen from FIG. 15 after applying a finer mesh to the cell C5 such that each sub-cell comprises only region of interest points or only polluting region points, according to one embodiment of the invention;

DETAILED DESCRIPTION

Figure 1:
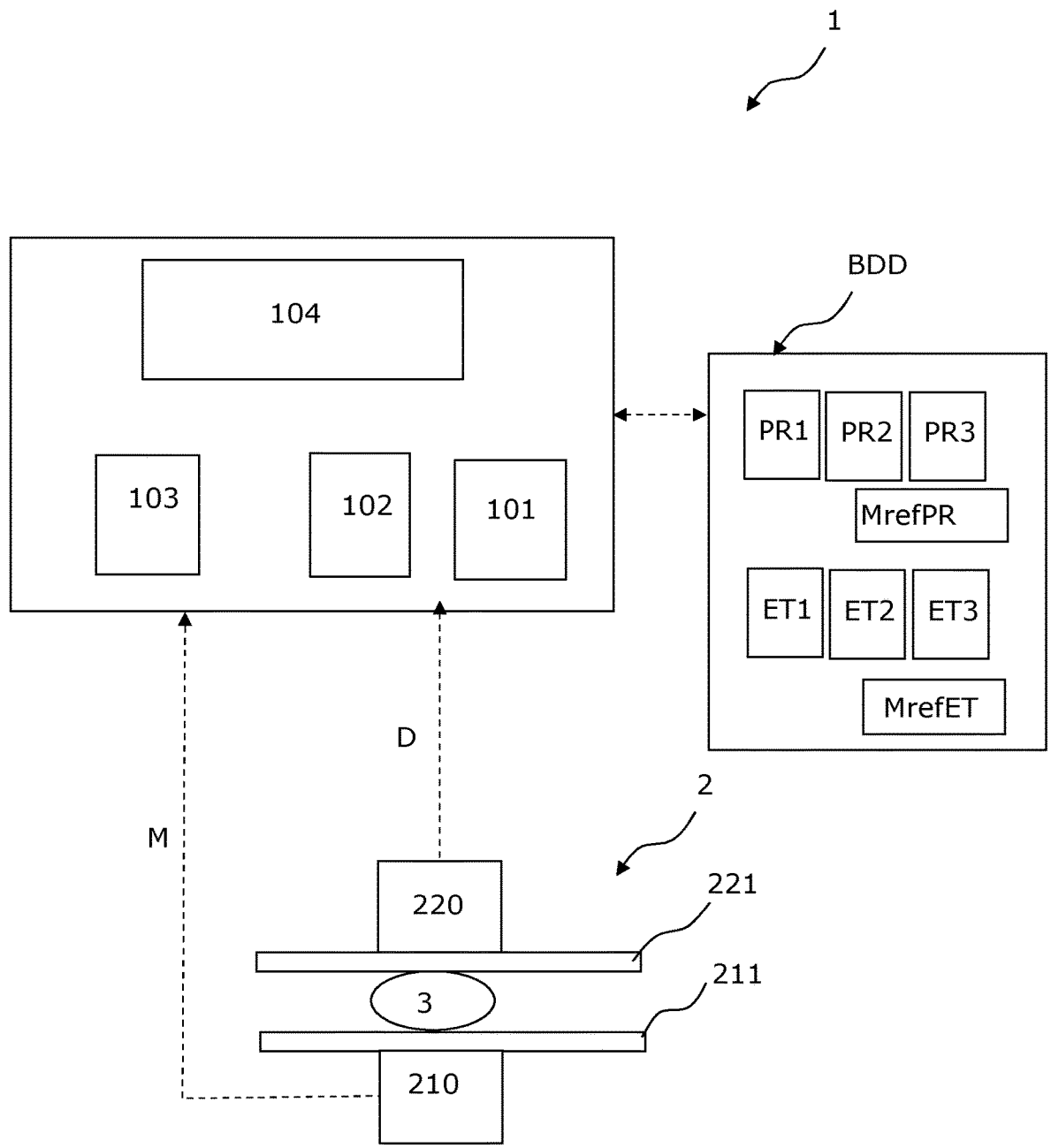
FIG. 1 is a schematic view of a computer system according to one embodiment of the invention.

The concept of the invention is described in more detail below with reference to the appended drawings, which show embodiments of the concept of the invention. In the drawings, the size and the relative sizes of the elements may be exaggerated for the sake of clarity. Similar numbers refer to similar elements throughout the drawings. However, this concept of the invention may be implemented in many different forms and should not be interpreted as being limited to the embodiments disclosed here. Instead, these embodiments are provided such that this description is complete, and communicate the scope of the concept of the invention to those skilled in the art. The following embodiments are discussed, for the sake of simplicity, in connection with the terminology and structure of an X-ray apparatus and an image processing system, in particular in the context of mammography.

Reference throughout the specification to "an/one embodiment" means that a particular functionality, structure or feature described in connection with an embodiment is included in at least one embodiment of the present invention. Thus, the occurrence of the expression "in one embodiment" in various places throughout the specification does not necessarily refer to the same embodiment. Furthermore, the particular functionalities, structures or features may be combined in any suitable manner in one or more embodiments.

The image processing described below is intended to mask certain areas of an image generated through 2D or 3D X-ray acquisition following the exposure of an object, such as a breast, to these X-rays. The masking is carried out in such a way as to keep the natural appearance of the object being viewed. The masking may be carried out irreversibly by replacing some sets of points in the image of the object with other sets of points, hereinafter called texturing elements, which are defined and stored independently of the image of the object. It is thus possible to make provision for these texturing elements to be present in memory, prior to acquiring the image of the object. In other words, a texturing element used to replace a given area (considered to be a polluting region) of the image is not initially generated from the content of the area to be replaced, nor from the content of another area of the original image. There may in particular be provision for the texturing elements to be defined based on areas of other images considered to be reference images.

Of course, and as explained below, if the texturing elements are not defined on the basis of the features of the areas of the image to be replaced, a texturing element is selected or generated from among the set of texturing elements while taking into account the features of the image area to be replaced. Moreover, after selecting or generating this texturing element, it may optionally be modified in order to be adapted depending on the area(s) adjacent to the area to be replaced, in particular in order to provide visual continuity between the replaced area and its environment.

The processing is in particular applicable to 2D and 3D X-ray images of elastic and deformable elements. As a variant, said object may be rigid or deformable, such as a lung, or more generally a ribcage, but not subjected to a compressive force during the image acquisition.

FIG. 1 illustrates a computer system 1 and an X-ray radiography apparatus 2.

As described below, the computer system 1 makes it possible to process one or more regions, called polluting regions, of a digital image of an object. In the remainder of the description, said object 3 is a breast and the image obtained using the X-ray apparatus 2 is a mammogram. Of course, the invention is applicable to other elastically compressible objects. As a variant, as recalled above, said object may be rigid or deformable, but not subjected to a compressive force during the image acquisition.

A polluting region is said to be "polluting" in the sense that it is not in itself of interest with regard to the image analysis that the radiologist has to perform, unlike other regions, called region of interest, which are of interest to the radiologist, for example in order to identify an anomaly.

One or more polluting regions of the image may interfere with the radiologist's analysis of one or more regions of interest by preventing him from concentrating his analysis on the region(s) of interest.

As described below, the invention makes it possible to preserve the or each region of interest and to limit the risk of the radiologist's analysis being interfered with by the presence of one or more polluting regions, while at the same time preserving the general graphic features of the breast (such as its shape, its texture) so as no longer to disrupt the operator through a graphic processing operation that would be inappropriate for the polluting region(s), as could be the case if the points of the polluting region(s) were to be simply assigned an identical intensity value or if the points of the polluting region(s) were to undergo a mathematical operation on their intensity values such that the modified region would preserve its polluting graphic features. For example, a region that might graphically show tissue corresponding to a healthy vessel in a breast and that might undergo reversible mathematical operations on these intensity values would preserve the general graphic appearance of this vessel, which would still risk interfering with the analysis of the image of the object. The solution according to the invention, which makes provision for masking by replacing the polluting region with a texturing element initially defined independently of this region, makes it possible, in the above example of a polluting region with a healthy vessel of a breast, to select a texturing element corresponding to breast fat and to substitute, possibly after modifying this texturing element, the points of the polluting region with the points of the texturing element, so as to visually show the breast fat instead of the healthy vessel. It is understood that, for a breast image, breast fat is a tissue type that will not draw the eye of the professional analyzing the image, unlike a vessel, such that the professional is able to concentrate his analysis on one or more regions of interest that are not subjected to such masking, that is to say that are not replaced with texturing elements.

Image Acquisition

The X-ray apparatus 2 is used to acquire an image of the breast 3 by exposing the breast 3 to X-rays (or X-ray beams). In particular, the apparatus 2 comprises compression plates 211, 221 between which the breast 3 is positioned. The breast 3 is then compressed between the compression plates 211, 221 under the effect of a given compressive force that is preferably adjustable.

An X-ray generator device 210 then generates X-rays to which the breast 3 is exposed. The generator device 210 may to this end comprise an X-ray emission tube and an electronic system for adjusting the energy or power, for example the voltage and the electric current, used to produce the X-rays.

A receiver device 220 receives the X-rays after they have passed through the breast 3. The receiver device 220 may also receive rays that pass around the object without passing through it and that then define the background of the image. The X-rays received by the receiver device 2 have different intensity values depending on the features of the various areas of the breast that are passed through, and thus make it possible to form an image IMG1 corresponding to the mammogram.

The points in the obtained image IMG1 correspond to points of the breast 3 that have been exposed to X-rays or to points of the environment of the breast 3 forming the background of the image. It should be noted that the images or image portions shown in FIGS. 2 to 16 are simplified diagrams in order to facilitate understanding of the processing method.

On the computer level, the image is represented by a set of defined points in space. The image may be characterized by all or some of its dimensions, such as width, height and depth.

Each point is characterized by coordinates, for example 2D (i.e. planar image), 3D (for example volume or 2D+time) or 4D (for example 3D volume+time) coordinates, and a numerical value associated with each point corresponding to a brightness value. The numerical values may be bounded. The numerical values may in particular belong to a subset of the space of natural or real numbers.

Numerous types of image acquisition are thus possible. By way of example, it is possible to distinguish between the following acquisitions:
  a 2D image;
  a plurality of 2D images acquired at different incidences where the angle of exposure is known, or at different incidences where the angle is not known;
  a 3D image.

For each type of acquisition, numerous acquisition parameters (i.e. metadata) may be provided. For example, all or some of the following parameters:
  the manufacturer and/or the model of the acquisition apparatus;
  the X-ray emission characteristics, such as power, duration, etc.
  the angle(s) of incidence of the acquisition;
  the thickness of the object under study, preferably under compression.

All or some of these parameters may be used as metadata associated with an acquired image.

In the remainder of the description, reference is made to an image, but the description of course also applies to a plurality of images. In particular, as recalled above, there may be provision for a plurality of images of the object to be acquired at various angles of exposure of the object to the X-rays, that is to say various angles of incidence of the rays in relation to the object.

The computer system comprises a data memory 103 storing data D of the image acquired using the receiver device 220. The data D may thus comprise, for each point P in the image, coordinates of said point and an intensity value $I_0$, called initial intensity value.

The computer system 1 also comprises a memory 101 containing program code instructions (computer instructions) for executing the steps of a method comprising steps as described below. A processor 102 makes it possible to execute said program code instructions.

As recalled above, the memory 103 makes it possible to store the image data D acquired using the receiver device 220. Metadata M presented below are also stored in the memory 103 or in another memory. The computer system may also comprise a display screen 104 for displaying the image.

The initial intensity $I_0$ of a point P in the image associated with a point of the breast 3 corresponds to the number of photons that have struck a corresponding point of the breast 3. Moreover, as explained above, each point P in the image is associated with metadata M. Thus, as illustrated schematically in FIG. 2, the acquired image IMG1 has points P with which there are associated coordinates, an initial intensity value Io and metadata M. One part 400 of the image IMG1 corresponds to the object 3 and another part 500 corresponds to the background of the image.

According to one preferred embodiment, the metadata M comprise:
the thickness of the breast 3 in the compressed state and the compressive force applied to the object,
the voltage and electric current values used to produce the X-rays.

As explained above, other metadata or additional metadata may be added, or certain metadata may be replaced with equivalent metadata. For example, the voltage and electric current values may be replaced with a variable representative of the power or energy used to generate the X-rays. Likewise, in the absence of the compression plates 221 and 222, the thickness of the compressed object may not be specified.

The metadata may be provided in full or in part by the apparatus 2 by connecting it to the computer system 1, or may be calculated from initial data. The metadata may also be entered by a user into the computer system 1 using a data entry interface, such as a keyboard or a touchscreen. The metadata may comprise what are called primary metadata provided during the acquisition of the image and what are called secondary metadata calculated from primary data, such as the initial intensity values and the primary metadata.

The metadata may also comprise the density of the breast 3. Density may be used to define subcategories from among a given category associated with a region of the image. There may be provision for the density to be a value calculated from the initial data, i.e. a value calculated from the intensity values and the metadata initially assigned to the acquired image.

Figure 2:
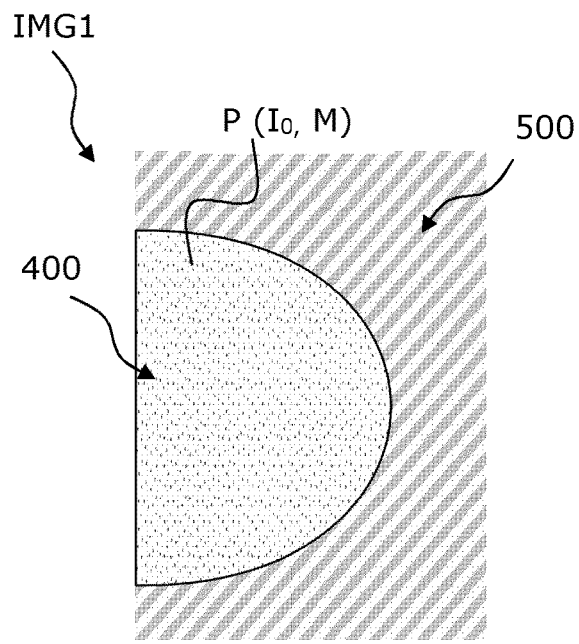
FIG. 2 is a schematic view of the image of a breast acquired using an X-ray apparatus according to one embodiment of the invention.

The part of the image that corresponds to the breast 3 is hereinafter called image 400 of the breast (see FIG. 2).

Figure 3:
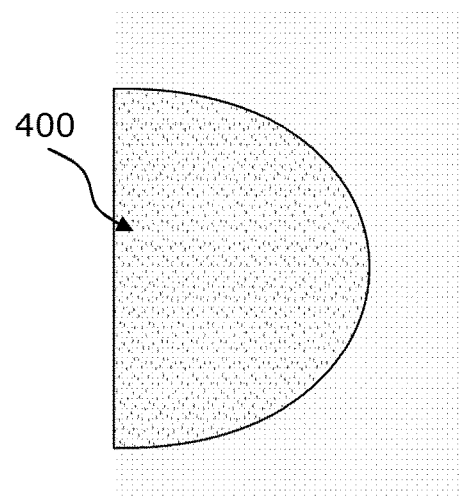
FIG. 3 is a schematic view of the image from FIG. 2 after removing the background of the image according to one embodiment of the invention.

According to one particular aspect and as illustrated schematically in FIG. 3, the part 400 of the image of the breast is isolated from the background 500 of the acquired image. The processing may thus be targeted on the part 400 of the image corresponding to the breast 3.

Polluting Region(s) and Region(s) of Interest

The initial intensity values $I_0$ of the points P in the image and said metadata M of the image are used to identify the polluting region(s) and the region(s) of interest.

Following the identification of a polluting region, a parameter with a value that corresponds to a category of non-interest, and possibly a subcategory, is then assigned to the points of said polluting region. Similarly, following the identification of a region of interest, a parameter with a value corresponding to a category of interest, and possibly a subcategory, is then assigned to the points of said region of interest.

After processing the points in the image, explained below, a new image IMG2 will be generated by replacing the initial intensity values $I_0$ of the points of the polluting regions with new intensity values (see FIG. 16).

According to one particular aspect, the replacement method, also called masking operation, corresponds to replacing the intensity values of the points in the areas of non-interest (also called polluting regions) with intensity values of image samples. These image samples may be texturing elements that are presented below, which may be chosen from among predefined texturing elements, or generated from other predefined texturing elements. The texturing elements, although they are initially independent of the acquired image, may furthermore be adapted according to features of the image or parts of the image, for example points of adjacent region(s) (which may be polluting or of interest) in order to ensure visual consistency.

Identification of Polluting Region(s) and Region(s) of Interest

In order to identify whether a group of points in the image (region of the image) corresponds to a polluting region or to a region of interest, the group of points in the image may be compared with other groups of reference points, for example the groups of points PR1, PR2, PR3, stored in a database BDD. These groups of points PR1, PR2, PR3 may correspond to image samples.

Each group of reference points PR1, PR2, PR3 stored in the database BDD comprises reference intensity values and reference metadata MrefPR, and is associated with a category corresponding to the polluting region type or to the region of interest type, and possibly with subcategories, for example a subcategory corresponding to a low-intensity region or a high-intensity region. Another example may be a subcategory, for example a region of interest subcategory, corresponding to a distribution of points describing a particular shape, for example a star shape. Advantageously, the same metadata are associated with the various points belonging to one and the same group of points, and each of the points has an intensity value that may be different from those of the other points.

The reference metadata MrefPR of the reference points PR1, PR2, PR3 preferably comprise metadata of the same type as the metadata associated with the acquired image IMG1. The reference metadata MrefPR may thus comprise, in a manner similar to the metadata associated with the acquired image:
a reference breast thickness value in the compressed state and a corresponding compressive force value,
one or more values of parameters(s) relating to the power or energy of X-rays, such as voltage and electric current values.

In particular, for a given group of points of a region, which, as described below, may correspond to a cell of the image, the system identifies a group of reference points from among the groups PR1, PR2, or PR3 stored in the database BDD, the metadata and point intensities of which most closely match the metadata and the initial intensities of the points of said group of points for which it is desired to identify the category.

Once a group of reference points has been identified whose features most closely match the features of said group of points to be categorized, said group of points to be categorized is assigned the category (polluting region or region of interest), and possibly the or each subcategory, of the identified group of reference points.

There may be provision for a group of points to be categorized (or the corresponding region) to inherit all or some of the metadata, and/or the category parameters, and possibly subcategory parameters, from the corresponding identified group of reference points.

A group of reference points that most closely matches a given group of points in the image may be identified using a correlation function.

By way of example, for a given group of points GP in the image having metadata $M_{GP}$ and a statistical moment of intensity S calculated from the intensity values of the points in said group, the system calculates, for the group of points GP, a score using an evaluation function $V(GP)=f(GP, M_{GP}, S)$.

A score V_PR_1, V_PR_2, V_PR_3 is also calculated for each reference region using this evaluation function. The system then evaluates an objective function or cost function L (GP, PR_i)=f (V(GP), V_PR_i) for each reference region. The group of reference points PR1, PR2, PR3 that gives the maximum or minimum value of the objective function or of the cost function will be chosen.

Figure 6:
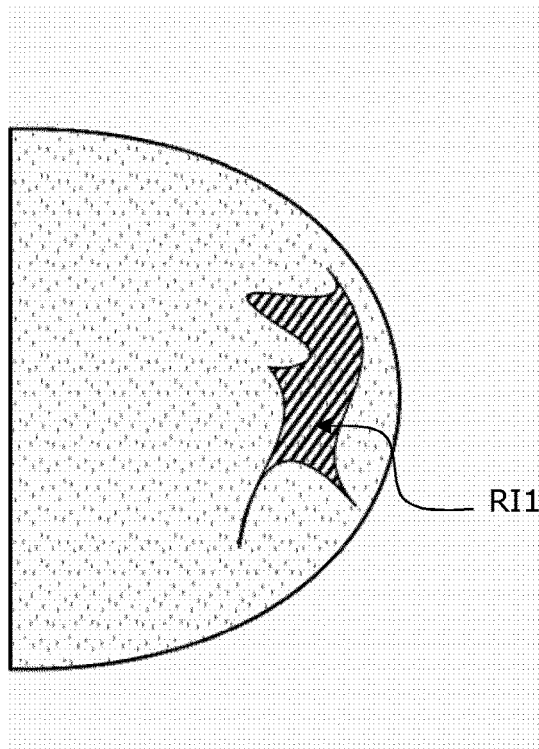
FIG. 6 is a schematic view of the image from FIG. 3 in which a region of interest is shown schematically, according to one embodiment of the invention.

In the example illustrated in the figures, the polluting regions (that is to say regions of non-interest) that are identified are the regions RP1, RP2 (see figure and the region of interest that is identified is the region RI1 (see FIG. 6). It will be understood that the presented method also applies to other image configurations having one or more polluting regions and one or more regions of interest.

Contour Region

Figure 4:
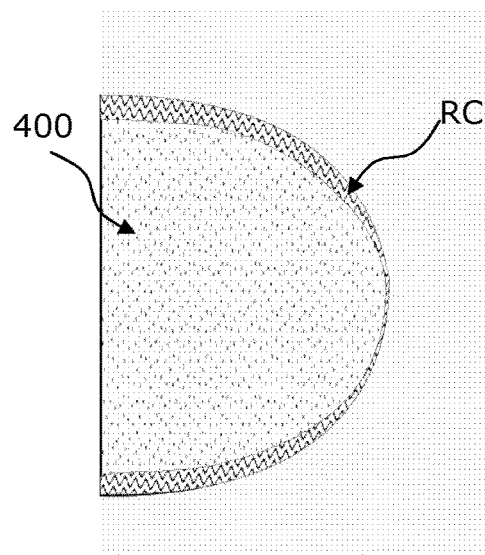
FIG. 4 is a schematic view of the image from FIG. 3 for which a determined contour area of the breast is shown schematically, according to one embodiment of the invention.
Figure 5:
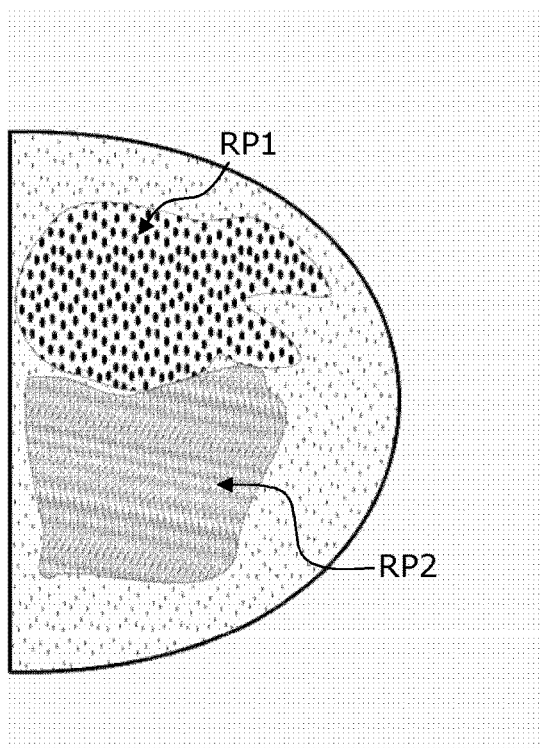
FIG. 5 is a schematic view of the image from FIG. 3 in which polluting regions are shown schematically, according to one embodiment of the invention.

According to one particular aspect and as illustrated in FIG. 4, a contour region RC of the image 400 of the breast 3, corresponding to a contour area of the breast 3, may be determined.

In the example of FIG. 4, the wider portions of the contour region RC correspond to parts of the breast in direct contact with the compression plates 211, 221.

A contour region RC may be determined by shape matching, and possibly on the basis of the intensity values of the contour area and of the force value applied to the breast 3.

Identification of Geometric Structures with a Particular Geometry or Shape

The system makes it possible to identify one or more geometric structures SGI1, SGP1 in the image 400 of the breast. A geometric structure comprises for example a linear structure.

Thus, in a first step, a geometric structure may be identified by its geometry, for example a broken or unbroken linear geometry. Next, the system searches for a correlation between the geometric structure and one or more regions of interest or one or more polluting regions (regions of non-interest). The correlation may depend on the brightness values, and possibly the metadata. The correlation function may be similar to the one presented above.

The system makes it possible, using a correlation function (for example similar to the one presented above), to assign an identified geometric structure a classification parameter having a first value, corresponding to a category of interest, when a correlation is established between said geometric structure and at least one region of interest. Conversely, a second value, corresponding to a category of non-interest (or polluting category), is assigned to the geometric structure when there is not any (sufficient) correlation between said geometric structure and the region(s) of interest.

Figure 7:
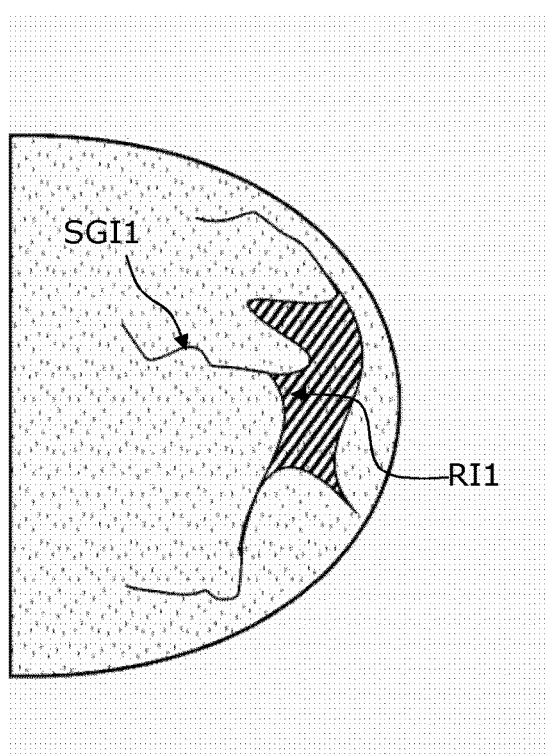
FIG. 7 is a schematic view of the image from FIG. 3 in which a geometric structure associated with a region of interest is shown schematically, according to one embodiment of the invention.
Figure 8:
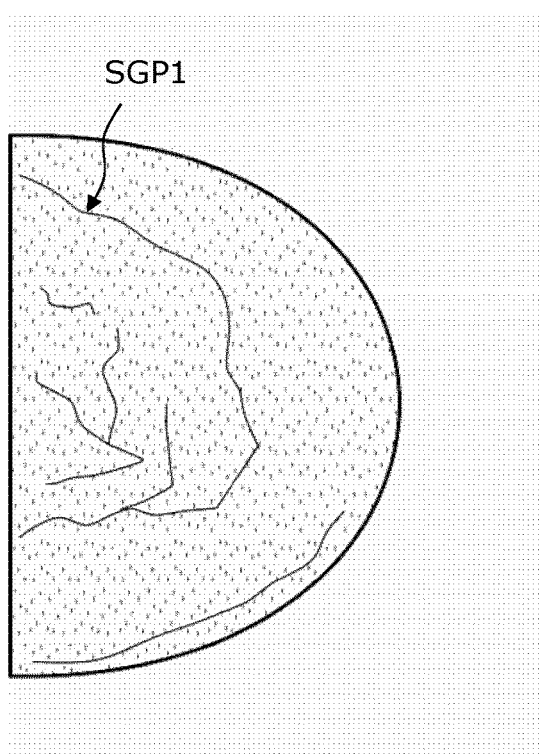
FIG. 8 is a schematic view of the image from FIG. 3 in which a geometric structure associated with one or more polluting regions is shown schematically, according to one embodiment of the invention.
Figure 9:
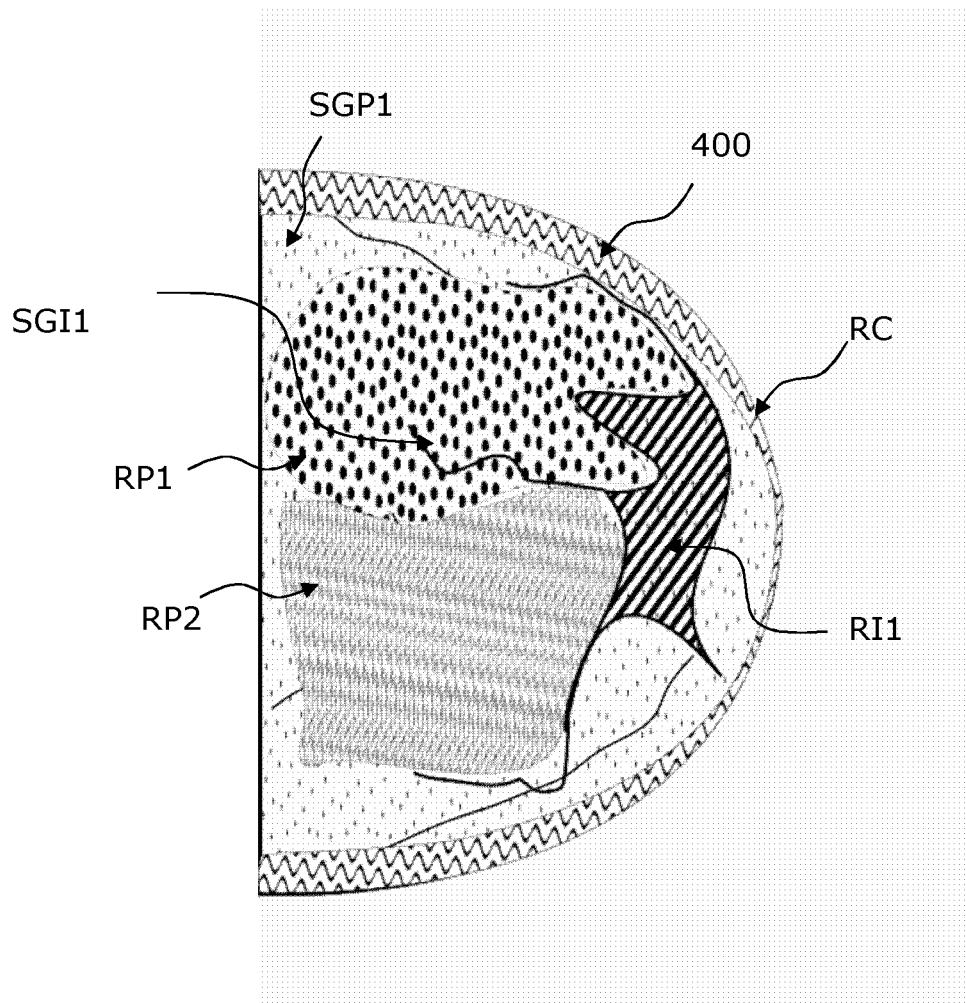
FIG. 9 is a schematic view of the image from FIG. 3 in which the polluting regions, the region of interest and the contour area and the geometric structures shown schematically in FIGS. 4 to 8 are shown schematically, according to one embodiment of the invention.

Thus, as illustrated in FIG. 7, the system identifies the geometric structure SGI1 for which a correlation is established with the region of interest RI1 such that a parameter corresponding to the category of interest is assigned to said geometric structure SGI1. As illustrated in FIG. 8, the system also identifies the geometric structure SGP1 for which a correlation is established with the polluting region RP1 such that a parameter corresponding to a category of non-interest is assigned to said geometric structure SGP1. There may be provision for the geometric structure to inherit all or some of the metadata, and/or the category parameters, and possibly subcategory parameters, of a region with which it is correlated.

Texturing Elements

To carry out the masking, use is made of texturing elements ET1, ET2, ET3 that are collected or defined beforehand. A texturing element is an X-ray image illustrating a part of an object of the same kind as the object, here the breast 3, the image of which has been acquired.

Said texturing element corresponds for example to the image of a fatty area that is less visually attractive and therefore less disruptive than an area of a polluting region. Thus, when these texturing elements, possibly after being modified, will be used to replace polluting regions of the image, in order to allow the radiologist to concentrate on the region(s) of interest, the breast will nevertheless retain its general features (shape and texture) so that the risk of these replacements disrupting the radiologist will be limited.

The texturing elements may be stored in a (local or remote) database accessible during the analysis, for example the database BDD.

Each texturing element ET1, ET2, ET3 comprises a group of points and metadata.

In a manner similar to the groups of reference points PR1, PR2, PR3, each texturing element ET1, ET2, ET3 comprises intensity values and reference metadata MrefET, and is possibly associated with a polluting region subcategory, for example a subcategory corresponding to a low-intensity region or a high-intensity region.

Advantageously, the same metadata are associated with the various points belonging to one and the same group of texturing element points, and each of the points has an intensity value that may be different from those of the other points.

The reference metadata MrefET of the texturing elements ET1, ET2, ET3 preferably comprise metadata of the same type as the metadata associated with the acquired image IMG1. The reference metadata MrefET may thus comprise, in a manner similar to the metadata associated with the acquired image:
 a reference breast thickness value in the compressed state and a corresponding compressive force value,
 one or more values of parameters(s) relating to the power or energy of X-rays, such as voltage and electric current values.

Various data may also be associated with each texturing element, such as the size of the texturing element, the tissue type or statistical intensity features. These data may also be associated with the reference points presented above.

According to one particular embodiment, the intensity variance (i.e. second mathematical moment) of one or each group of reference points is higher than that of one or each texturing element. In other words, a texturing element may have greater homogeneity of intensity than a group of reference points.

According to one particular embodiment, the average of the intensity values (i.e. first mathematical moment) of the points of one or each group of reference points is higher than that of one or each texturing element.

It is understood that the texturing elements are different from the groups of reference points that are used to identify the polluting regions or regions of interest.

According to one preferred embodiment, the aim of the masking operation is to make one or more what are called polluting regions invisible to the operator and to replace them with regions that make it possible to reduce attention during the image analysis. The texturing elements are thus selected and classified in terms of their intensity properties, in particular the intensity values of the element points and of the associated mathematical moments. The statistical distribution of the points of a texturing element may furthermore be taken into account in order to determine the tissue type represented by said texturing element.

A polluting region may be masked by applying a mask formed from one or more texturing elements to all or part of said polluting region.

Selection or Generation of Texturing Elements

For an identified polluting region RP1, RP2, at least one mathematical moment of the intensity values of the points of said region, such as the average intensity value $I_{avg}$ or the intensity variance, is calculated. Various mathematical moments may be calculated and taken alone or in combination in order to identify a polluting region. Similarly, one or more mathematical moments may be calculated for cells in the vicinity of said polluting region.

Texturing elements ET121; ET133 are selected from among a plurality of predefined texturing elements ET121, ET122, ET123; ET131, ET132, ET133 on the basis of features, such as one or more calculated mathematical moments of the polluting region and preferably of one or more associated items of metadata, and optionally on the basis of the mathematical moments in the vicinity of said region.

In particular, for a given group of points of a region, which, as explained below, may correspond to a cell of the image, following the application of a grid to the image, there may be provision for the system to select a texturing element from among the predefined texturing elements in the database BDD, the metadata and point intensities of which most closely match the metadata and the initial intensities of the points of the polluting region and possibly its vicinity. The correlation between the texturing elements and the polluting region may be established by analyzing an objective function or a cost function taking into account some or all of the metadata and the initial intensities of said region. To this end, it is possible to use correlation and objective or cost functions that may be similar to those presented above.

There may also be provision for a new texturing element to be generated on the basis of a plurality of texturing elements identified for example on the basis of the corresponding mathematical moments of intensity.

Once the texturing element has been selected or generated from selected texturing elements, the system uses this texturing element as a mask for modifying a group of points of the polluting region. In particular, the system may modify the intensity values of the points in this group on the basis of the intensity values of the points of said texturing element. This modification may be replacing the intensity values of the points in this group with the intensity values of the points of said texturing element. The intensities of the other groups of points of the region may also be modified on the basis of, or replaced with, the intensities of the groups of points of the texturing element.

The features of the texturing element used as a mask may be adapted (that is to say modified), for example on the basis of one or more areas adjacent to the or each area where the mask is applied, so as not to deviate from the general features (intensity, texture) of the acquired image.

According to one preferred embodiment, the masking of what are called the "polluting" regions of non-interest is intended to replace said regions with a mask constructed from texturing elements or from the compositions of said texturing elements.

In one preferred embodiment, the texturing elements forming the mask exhibit specific intensity features.

By way of example, there may be provision for the minimum image intensity value to correspond to air.

The texturing elements may be selected or generated from selected texturing elements so as to minimize the average intensity (i.e. first mathematical moment) by approaching a predefined threshold, denoted $M_{min}$, different from the absolute minimum (for example intensity of air), and so as to minimize the standard deviation of the intensity values (that is to say to maximize the homogeneity) by approaching a threshold other than zero, denoted $S_{min}$. According to such an embodiment, only the texturing elements are subjected to constraints on one or more of their mathematical moments.

According to one particular embodiment, a group of reference points PR_i may have the same statistical features as at least one texturing element.

Breaking of the Object of the Image Down into Cells

Figure 10:
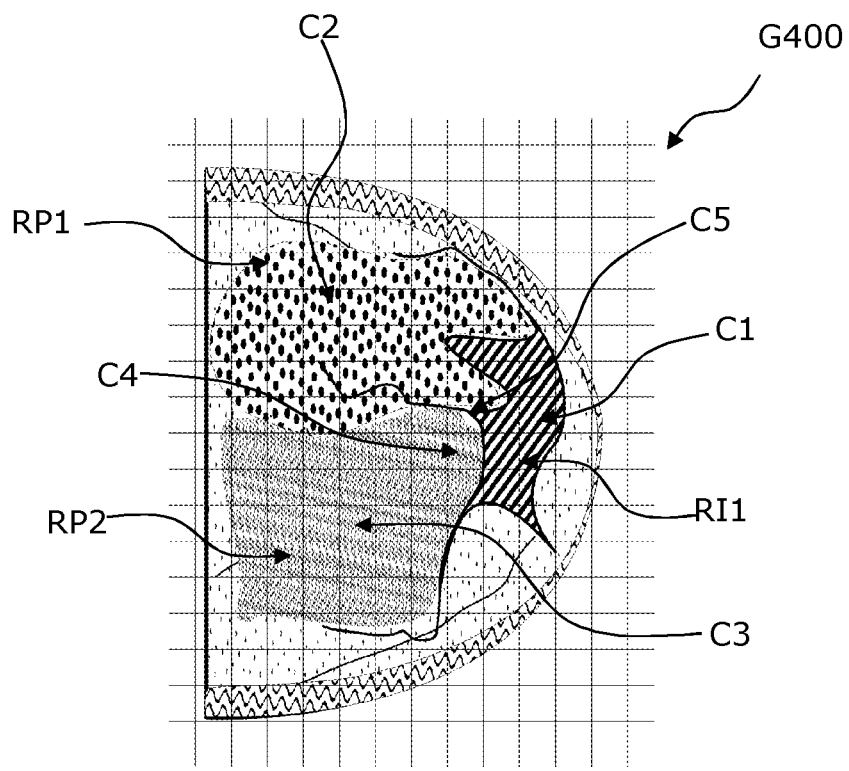
FIG. 10 is a schematic view of the image from FIG. 9 with a grid applied thereto in order to break the image down into cells, according to one embodiment of the invention.

The image 400 of the breast is broken down into blocks of adjacent points, called cells C1, C2, C3, C4, C5 (FIG. 10).

The cells resulting from the breaking down of the image result from the application, to the image, of a grid G400 having a mesh of predefined size.

Initially, the mesh of the grid, and therefore the dimensions of the cells, may be chosen so as to correspond to the dimensions of the largest texturing elements that are used. If necessary, a grid with a finer mesh may be applied thereafter to the image or part of the image, for example to a given cell, so as to allow the use of smaller texturing elements.

Composition of the Cells

There may in particular be provision, when a cell, for example the cell C5 as illustrated in FIG. 10, contains points of various region categories, or of various sub-categories, for example points of a region of interest RI1 and of a polluting region RP1, RP2, or else points of two different polluting regions, for the corresponding cell to be broken down into sub-cells.

Thus, as illustrated in FIG. 15A, the cell C5 is broken down into sub-cells C51, which may themselves be broken down into sub-cells until each sub-cell contains only points of a region of interest RI1 or only points of a polluting region RP1, RP2 (FIGS. 15 and 15A). The processing steps presented in this description are then applied to these sub-cells.

FIG. 15A thus illustrates the application of a finer mesh to the cell C5, such that each sub-cell C51 comprises only points of a region of interest or only points of a polluting region. It will be possible to consider that a cell comprises "only" points of a given region when the proportion in the cell of these points belonging to a given region is higher than a given threshold value, for example 95%.

In other words, the cell is broken down into a grid with the smaller mesh in order to perform finer analysis.

Such a breakdown may be gradual and carried out several times. Upon each new iteration, the content of the cells is analyzed in order to identify any need for additional breakdown.

Region of Interest Cell

Figure 11:
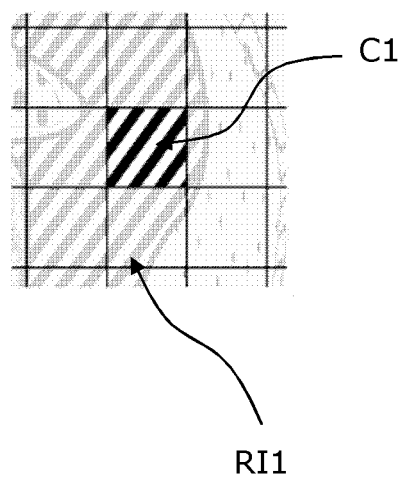
FIG. 11 is a view of part of the image from FIG. 10 showing a cell C1 of a region of interest and adjacent cells, according to one embodiment of the invention.

When each of the points in a cell C1 belongs to a region of interest RI1, said points remain unchanged in the generated new image IMG2 (FIG. 11). In particular, said points remain unchanged regardless of whether points in adjacent cells belong to a polluting region or to a region of interest.

Processing of Polluting Region Cells

When each of the points in a cell belongs to a polluting region and the points in the adjacent cells also belong to said polluting region, said points in the cell are replaced with the points of a texturing element chosen from among a plurality of predefined texturing elements.

Thus, as illustrated in FIG. 12, the cell C2 is surrounded by adjacent cells that also belong to the polluting region RP1. The system determines, from among a plurality of texturing elements ET121, ET122, ET123, the texturing element ET121 that most closely matches the cell C2 on the basis of intensity values and the metadata associated with the points in the cell and the texturing elements. Similarly, the cell C3 illustrated in FIG. 13 is surrounded by adjacent cells that also belong to the polluting region RP2. The system determines, from among a plurality of texturing elements ET131, ET132, ET133, the texturing element ET133 that most closely matches the cell C3 on the basis of intensity values and the metadata associated with the points in the cell and the texturing elements.

When each of the points in a cell belongs to a polluting region and the points in at least one adjacent cell belong to a category other than said polluting region, for example to a region of interest or to another polluting region, a new texturing element is generated from at least one, preferably a plurality of, predefined texturing elements, and on the basis of the points in said at least one adjacent cell. There may in particular be provision for one of the texturing elements used to generate the new texturing element to be chosen on the basis of said points in said at least one adjacent cell. The points in said cell are replaced with the points of said new texturing element. Advantageously, a new texturing element is generated from a predefined texturing element chosen on the basis of the features of said cell to be processed and from another texturing element chosen on the basis of the features of said at least one adjacent cell.

Thus, as illustrated in FIG. 14, each of the points in the cell C4 belongs to the polluting region RP1, while the adjacent cell CV4 comprises points that belong to the region of interest RI1.

A new texturing element ET143 is then generated from the predefined texturing element ET141 that closely matches the cell C4, and from the texturing element ET142 that closely matches the point(s) in the adjacent cell CV4. The points in said cell C4 are then replaced with the points of said new texturing element ET143 (FIGS. 14, 14A and 14B). The points of said texturing element ET143 used as a mask for the cell C4 may also be adapted on the basis of the surroundings of the cell C4.

Resulting Image

Figure 16:
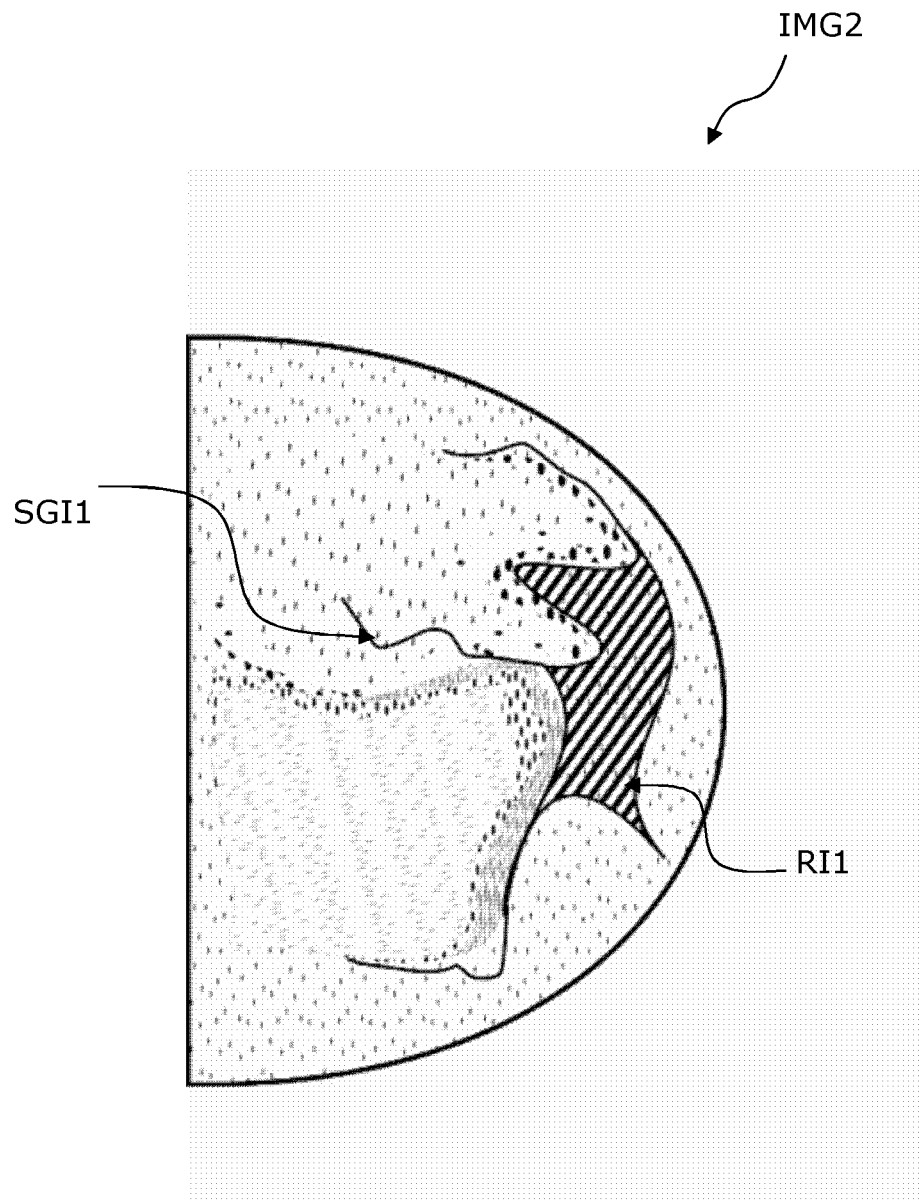
FIG. 16 is a view of an image generated from the image of FIG. 10 after modifying polluting regions using texturing elements, according to one embodiment of the invention.

As illustrated in FIG. 16, the region of interest RI1 as well as the geometric structure of interest SGI1 that is associated therewith are preserved, while the original polluting regions RP1, RP2 have been modified using the texturing elements to blend these regions into their environment and thus no longer risk attracting the radiologist's attention. It may be noted in the example illustrated in FIG. 16 that the area of the region referenced RP2 in FIG. 5, close to the region of interest or to the polluting region referenced RP1 in FIG. 5, has been modified differently from the rest of the region RP2 in order to preserve the general shape and texture of the object and to ensure appropriate region transitions, so as not to generate visual disruptions.

The radiologist is thus able to concentrate his analysis on the region of interest RI1 and the geometric structure of interest SGI1 that is associated therewith.

The described functions and steps may be implemented in the form of a computer program or via hardware components (for example programmable gate arrays). In particular, the functions and steps carried out by the computer system 1 may be performed by sets of instructions or computer modules implemented in a processor or controller or be performed by dedicated electronic components or FPGA or ASIC components. It is also possible to combine computer parts and electronic parts.

When it is stated that the computer system is configured so as to perform a given operation, this means that the system comprises computer instructions and the corresponding execution means that make it possible to perform said operation and/or that the system comprises corresponding electronic components.

The invention is not limited to the embodiments illustrated in the drawings.

In addition, the term "comprising" does not rule out other elements or steps. In addition, features or steps that have been described with reference to one of the embodiments disclosed above may also be used in combination with other features or steps of other embodiments disclosed above.

The invention claimed is:

1. A method, implemented using a computer system, for processing at least one part, called polluting region, of a digital image of an object, the image being produced from an X-ray apparatus by exposing the object to X-rays, said image being stored in a data memory and comprising:
points with each of which there is associated a numerical intensity value, called initial intensity $I_0$, which corresponds to the number of photons that have struck a corresponding point of the object, and
at least one item of metadata,
wherein said at least one item of metadata comprises at least one of the following items of metadata:
one or more physical parameters of the object, such as the thickness of the object,
one or more parameters relating to the power or the energy of the X-rays with which the image was acquired, such as the voltage and electric current values used to produce the X-rays;
said method comprising:
identifying at least one group of points in the image corresponding to a polluting region on the basis of the initial intensity values $I_0$ of the points in the image and of said at least one item of metadata;
generating a new image comprising a step of replacing the initial intensity values $I_0$ of at least some of the points of said at least one polluting region with new intensity values
said method further comprising:
providing a set of groups of points, called texturing elements, stored in a data memory, each texturing element comprising a plurality of points and intensity values associated with the points, and
wherein the step of replacing the initial intensity values $I_0$ of at least some of the points of said at least one polluting region with new intensity values comprises:
selecting a texturing element from among a plurality of texturing elements or generating a new texturing element from one or more selected texturing elements, and
replacing the initial intensity values $I_0$ of at least some of the points of said at least one polluting region with the intensity values of at least some of the points of the selected texturing element or of the generated new texturing element.

2. The method as claimed in claim 1, wherein the method also comprises identifying at least one group of points in the image corresponding to a region of interest on the basis of the initial intensity values $I_0$ of the points in the image and of said at least one item of metadata.

3. The method as claimed in claim 1, wherein the step of identifying at least one group of points in the image as a polluting region comprises comparing these points in the image with other groups of reference points stored in a database, each group of reference points being associated with at least one item of metadata, called reference item of metadata.

4. The method as claimed in claim 1, wherein each texturing element comprises at least one item of metadata and the texturing element is selected or the new texturing element is generated on the basis of said at least one item of metadata.

5. The method as claimed in claim 1, wherein, for an identified polluting region, the method comprises:
calculating at least one mathematical moment from the intensity values, such as the average intensity value $I_{avg}$ or the intensity variance, of the points in at least one part of said identified polluting region,
selecting a group of points, called texturing element, from among a plurality of predefined texturing elements, or generating a new texturing element from one or more selected texturing elements,
the texturing element being selected or generated on the basis of said at least one calculated mathematical moment, such as said average intensity value $I_{avg}$ or said intensity variance, of the points in said at least one part of the polluting region, the points of said selected texturing element or of said generated new texturing element having a set of given intensity values different from that of the points in said at least one part of said identified polluting region;
and in that at least some of the points of said selected texturing element or of said generated new texturing element replace the points in said at least one part of the identified polluting region.

6. The method as claimed in claim 1, wherein the selected texturing element or the generated new texturing element has an item of metadata corresponding to a tissue type, for example fat, which is different from the tissue type, for example a blood vessel, of the polluting region to be replaced.

7. The method as claimed in claim 1, wherein said at least one item of metadata associated with the image comprises an item of metadata defined by correlation with at least one part of another image of the object, for example acquired at a different incidence or at a different time.

8. The method as claimed in claim 1, wherein said replacement step, also called masking operation, comprises breaking the image of the object down into blocks of adjacent points, called cells.

9. The method as claimed in claim 8, wherein, when each of the points in a cell belongs to a region of interest, said points remain unchanged in the generated new image.

10. The method as claimed in claim 8, wherein, when the points in a cell belong to a polluting region and the points in the adjacent cells also belong to said polluting region, said points in the cell are replaced with the points of a texturing element selected from among a plurality of predefined texturing elements.

11. The method as claimed in claim 10, wherein the selection of said texturing element depends on the intensity values of said points in the cell.

12. The method as claimed in claim 8, wherein, when the points in a cell belong to a polluting region and the points in at least one adjacent cell belong to a category other than said polluting region, for example to a region of interest or to another polluting region, a new texturing element is generated from one or more predefined texturing elements, and on the basis of the points in said at least one adjacent cell, the points in said cell being replaced with the points of said new texturing element.

13. The method as claimed in claim 8, wherein, when a cell contains both points of a region of interest and of a polluting region, the cell is broken down into sub-cells, which may themselves be broken down into sub-cells until each sub-cell contains only points of a region of interest or only points of a polluting region.

14. The method as claimed in claim 1, wherein the method comprises a step of processing the acquired image in which the part of the image corresponding to the object, called image of the object, is isolated from the background of the acquired image.

15. The method as claimed in claim 1, wherein the method comprises a step of determining a region, called contour region, corresponding to a contour area of the object.

16. The method as claimed in claim 1, the method comprises identifying, in the image part corresponding to the object, at least one geometric structure, for example a linear structure,
and in that the method comprises assigning said at least one identified geometric structure a classification parameter having a first value, corresponding to a category of interest, when a correlation is established between said geometric structure and at least one region of interest; and a second value, corresponding to a category of non-interest, when there is no correlation between said geometric structure and the region(s) of interest.

17. The method as claimed in claim 1, wherein, with the object being able to be compressed under the effect of a given compressive force, said at least one item of metadata comprises the thickness of the object in the compressed state and the compressive force applied to the object.

18. A non-transient computer program product comprising program code instructions for executing the steps of a method as claimed in claim 1 when said program is executed by a processor of a computer system.

19. A computer system comprising a memory containing program code instructions for executing the steps of a method as claimed in claim 1, a processor for executing said program code instructions, a memory for storing image data and metadata, and preferably a display screen.

20. An installation comprising a computer system as claimed in claim 19, and an X-ray apparatus, said apparatus comprising an emitter device able to emit an X-ray beam and a receiver device able to receive the X-rays emitted by the emitter device after they have passed through the object,
and the X-ray apparatus being configured so as to transmit, to the computer system, image data corresponding to the X-rays received by the receiver device after they have passed through the object, and optionally metadata comprising for example one or more parameters relating to the power or to the energy of the X-rays produced.

* * * * *